United States Patent [19]

Ikekawa

[11] Patent Number: 4,711,881
[45] Date of Patent: Dec. 8, 1987

[54] 1α,25-DIHYDROXY-26,27-DIMETHYL-CHOLECALCIFEROL AND ITS USE IN THE TREATMENT OF CALCIUM PATHOBOLISM

[75] Inventor: Nobuo Ikekawa, Musashino, Japan

[73] Assignee: Taisho Pharmaceutical Co., Ltd., Tokyo, Japan

[21] Appl. No.: 763,568

[22] Filed: Aug. 7, 1985

[30] Foreign Application Priority Data

Aug. 10, 1984 [JP] Japan .................. 59-167552

[51] Int. Cl.[4] .................. A61K 31/59; C07J 9/00
[52] U.S. Cl. .................. 514/167; 260/397.2
[58] Field of Search .................. 260/397.2; 514/167

[56] References Cited

U.S. PATENT DOCUMENTS

| | | | |
|---|---|---|---|
| 3,697,559 | 10/1972 | De Luca et al. | 260/397.2 |
| 4,004,003 | 1/1977 | Babcock et al. | 514/167 |
| 4,367,177 | 1/1983 | De Luca et al. | 260/397.2 |
| 4,388,243 | 6/1983 | Nishikawa et al. | 260/397.2 |

Primary Examiner—Leonard Schenkman
Assistant Examiner—Joseph A. Lipovsky
Attorney, Agent, or Firm—Wenderoth, Lind & Ponack

[57] ABSTRACT

1α,25-Dihydroxy-26,27-dimethylcholecalciferol represented by formula:

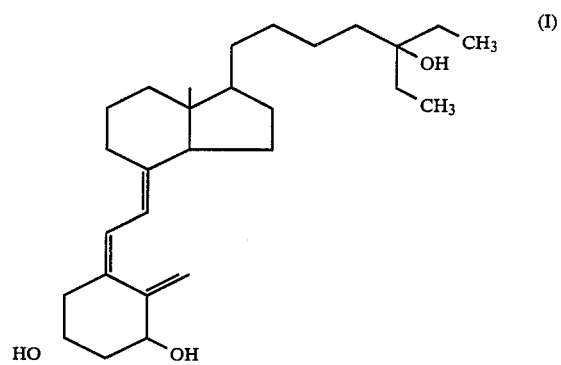

This compound is prepared by irradiating 26,27-dimethylcholesta-5,7-diene-1α,3β,25-triol with ultraviolet light, and is useful for the prevention or treatment of calcium pathobolism or osteoporosis.

3 Claims, No Drawings

1α,25-DIHYDROXY-26,27-DIMETHYLCHOLECALCIFEROL AND ITS USE IN THE TREATMENT OF CALCIUM PATHOBOLISM

This invention relates to a derivative of vitamin $D_3$, i.e. cholecalciferol, and more specifically to 1α,25-dihydroxy-26,27-dimethylcholecalciferol represented by formula,

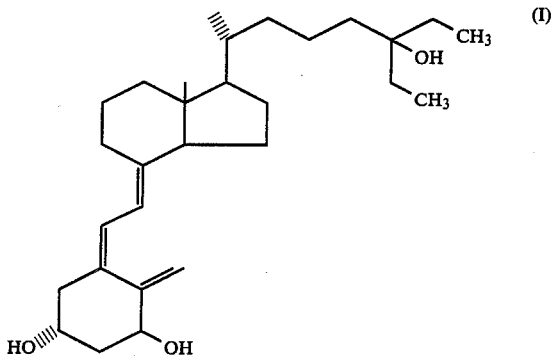

a process for producing same, medicaments of said compound, and use of said compound as an active component in medicaments for the prevention or treatment of diseases such as calcium pathobolism and osteoporosis in particular.

Vitamin $D_3$ or cholecalciferol is a well-known agent for the control of calcium and phosphorus homeostasis. In the normal animal or human, this compound is known to stimulate calcium transport and bone-calcium mobilization and is effective in preventing rickets.

It is also now well known that to be effective, vitamin $D_3$ must be converted in vivo to its hydroxylated forms. For example, the vitamin is first hydroxylated in the liver to form 25-hydroxyvitamin $D_3$ and is further hydroxylated in the kidney to produce 1α,25-dihydroxyvitamin $D_3$ or 24R,25-dihydroxyvitamin $D_3$. The 1α,25-dihydroxylated form of the vitamin is generally considered to the physiologically-active or hormonal form of the vitamin and to be responsible for what are termed the vitamin D-like activities such as increasing intestinal absorption of calcium and phosphate and mobilizing bone mineral.

Such active vitamin $D_3$ is a medicament indispensable for the prevention or treatment of diseases such as chronic renal insufficiency, hypoparathyroidism, rickets, osteoporosis, etc. Moreover, it has lately attracted attention for the possibility as an anticancer agent and differentiation inducer for cancer, and a vitamin $D_3$ homologue has been increasingly studied.

For instance, U.S. Pat. No. 4,225,596 discloses that 1α-hydroxycholecalciferol, 1α-hydroxyergocalciferol, 1,25-dihydroxycholecalciferol, 1,25-dihydroxyergocalciferol or 1,24,25-trihydroxycholecalciferol is useful for the prevention or treatment of metabolic bone disease, and U.S. Pat. No. 4,397,847 discloses that 24,24-difluoro-1α,25-dihydroxycholecalciferol is employed to treat osteoporosis.

During the study of high active vitamin $D_3$ derivatives, the present inventor has discovered that when methyl groups are introduced into the 26- and 27-positions of 1α,25-dihydroxyvitamin $D_3$, there can result a vitamin $D_3$ homologue having quite high activity and less toxicity, and he has completed the present invention.

Thus, the present invention is to provide 1α,25-dihydroxy-26,27-dimethylcholecalciferol having the structure of formula (I) as a novel compound.

The compound of formula (I) can be produced from 1α,3β-di(lower alkanoyloxy)chol-5-en-24-ol [compound A] as follows.

The term "lower" used in the specification means that the number of carbon atoms in a group or compound to which this term is given is not more than 6, preferably not more than 4. Thus, examples of a "lower alkanoyloxy" are acetoxy, propionyloxy, butyryloxy, etc. Of these, acetoxy is preferable. Moreover, examples of a "lower alkyl" are methyl, ethyl, propyl, isopropyl, butyl, sec-butyl, isobutyl, tert-butyl, etc. Especially, methyl is preferable.

First, an alcohol moiety in the 24-position of 1α,3β-di(lower alkanoyloxy)chol-5-en-24-ol [compound A] is oxidized into an aldehyde group. The oxidation can be conducted in a suitable solvent using an oxidizing agent. Examples of the suitable solvent include hydrocarbons and halogenated hydrocarbons such as heptane, benzene, toluene, chloroform and methylene chloride, ethers such as diethyl ether and tetrahydrofuran, acetone and dimethylformamide.

Examples of the oxidizing agent include oxidizing agents commonly used to convert a primary alcohol into an aldehyde, such as chromic acid compounds such as pyridinium chlorochormate and pyridinium dichromate, manganese dioxide, silver carbonate-selite, and dimethyl sulfoxide-dicyclohexylcarbodiimide. Of these, the chromic acid compounds such as pyridinium chlorochromate and pyridinium dichromate are especially preferable.

The temperature of the above oxidation reaction can commonly be in the range of from $-20°$ to $100°$ C. depending on type of the oxidiaing agent, and a suitable amount of the oxidizing agent is generally 1 to 3 mol equivalents per mol of the starting compound A.

In this way, 1α,3β-di(lower alkanoyloxy)-26,27-dinorcholest-5-en-24-al [compound B] results.

Next, the resulting compound B is subjected to the Wittig reaction and the subsequent hydrolysis to form 1α,3β-di(lower alkanoyloxy)-26,27-dinorcholest-5-en-25-al [compound C].

In the Wittig reaction of the compound B, the aldehyde group in the 24-position is converted into a lower alkoxymethylene group, e.g. a methoxymethylene group. The Wittig reaction can be carried out in a usual manner by mixing a lower alkoxymethyltriarylphosphonium halide such as methoxymethyltriphenylphosphonium chloride with n-butyl lithium in a solvent, adding the compound B to the mixture and reacting them at temperatures of from $-20°$ to $80°$ C., usually about room temperature. Examples of the above solvent are ethers such as diethyl ether and tetrahydrofuran, and hydrocarbons such as hexane, benzene and toluene. Depending on the conditions of the Wittig reaction, the lower alkanoyloxy groups in the 1-position and/or 3-position of the compound C are reacted at the same time to form corresponding 1α- and/or 3β-hydroxy compound. On this occassion, the hydroxyl group(s) can be converted again into lower alkanoyloxy group(s).

The thus obtained 24-lower alkoxymethylene compound is then hydrolyzed into the compound C. The hydrolysis can generally be effected at temperatures in the range of from about $0°$ C. to a boiling point of a solvent, usually about room temperature in a suitable solvent using a suitable acid in an appropriate amount of from a catalytic amount to an excessive amount. Examples of the suitable solvent are hydrocarbons such as hexane, heptane, benzene and toluene, halogenated hydrocarbons such as chloroform and methylene chloride and ethers such as diethyl ether, tetrahydrofuran and dioxane. Examples of the suitable acid are mineral acids such as hydrochloric acid and sulfuric acid, and organic acids such as p-toluene sulfonic acid and acetic acid.

The compound C obtained by the above hydrolysis is then subjected to the oxidation of the aldehyde group in the 15-position. This oxidation can commonly be carried out by treating the compound C with an oxidizing agent in a suitable solvent. Examples of the suitable solvent are hydrocarbons and halogenated hydrocarbons such as hexane, heptane, benzene, chloroform and methylene chloride, ethers such as diethyl ether and tetrahydrofuran, acetone and dimethylformamide. Examples of the oxidizing agent include those ordinarily empolyed to oxidize the aldehyde group into the carboxyl group, such as Jones reagent, Collins reagent, silver oxide and selenium dioxide.

These oxidizing agents can be used in a proportion of 1 to 3 equivalents, usually about 1 equivalent per mol of the compound C. The reaction sufficiently advances at about room temperature, yet sometimes it can be effected with heating at a temperature up to a boiling point of the solvent.

Thus, $1\alpha,3\beta$-di(lower alkanoyloxy)-26,27-dinorcholest-5-en-25-oic acid [compound D] is formed and then converted into a lower alkyl ester. The compound D can be esterified by an esterification method known per se. It can be readily conducted through, for example, a method by a reaction with a diazoalkane such as diazomethane, a method wherein an alkyl halide such as methyl iodide is reacted in the presence of a base such as sodium hydroxide, potassium hydroxide, sodium carbonate, triethylamine, or pyridine. The esterification is preferably carried out by the former diazoalkane method.

The esterification reaction gives an ester corresponding to the above compound D, i.e. $1\alpha,3\beta$-di(lower alkanoyloxy)-26,27-dinorcholest-5-en-25-oic acid lower alkyl ester [compound E].

Following the Grignard reaction, the compound E is then reacted with an ethylmagnesium halide under conditions known per se to form 26,27-dimethylcholest-5-ene-$1\alpha,3\beta,25$-triol [compound F]. The compound F is then converted to a lower alkanoylated compound, i.e. $1\alpha,3\beta$-di(lower alkanoyloxy)-26,27-dimethylcholest-5-en-25-ol [compound G] by the method as follows. The $1\alpha$- and $3\beta$-hydroxyl groups are protected by lower alkanoyl groups, followed by introduction of a double bond between the 7- and 8-position and removal of the protective groups in the 1- and 3-positions.

The introduction of the double between the 7- and 8-position of the compound G can be conducted by, for example, heating the compound G in an inert solvent together with a nearly equimolar amount or a somewhat excessive molar amount of N-bromosuccinimide to brominate the 7-position, and then reacting the bromide with tetra-n-butylammonium halide to remove hydrogen bromide.

The removal of the protective group in the thus formed $1\alpha,3\beta$-di(lower alkanoyloxy)-26,27-dimethylcholesta-5,7-dien-25-ol [compound H] can readily be carried out by e.g. treating the compound H with an alcohol solution of an alkalimetal hydroxide such as potassium hydroxide or sodium hydroxide in a usual manner.

The resulting 26,27-dimethylcholesta-5,7-diene-$1\alpha,3\beta,25$-triol [compound J] can be formed into $1\alpha,25$-dihydroxy-26,27-dimethylcholecalciferol of formula I by irradiation of ultraviolet light.

The ultraviolet light irradiation of the compound J can be carried out by dissolving the compound J in a suitable solvent, preferably a low-boiling solvent, and irradiating the solution with ultraviolet light. Examples of the suitable solvent are hydrocarbons such as hexane, octane and benzene, ethers such as diethyl ether and tetrahydrofuran, alcohols such as methanol and ethanol, preferably a lower alkanol, and mixtures thereof. An effective wavelength of ultraviolet light for irradiation is from 200 to 360 nm. Lights for any light sources are available if they include the ultraviolet light having the wavelength in the above range. Suitable examples of the irradiation light sources are a medium-pressure mercury lamp, high-pressure mercury lamp and laser. If required, unwanted lights may be cut through a filter. The time for irradiation of ultraviolet light varies with an intensity of a lamp as a light source and a reaction scale, and is properly selected between several tens of seconds and several hours.

Said irradiation is performed at temperatures in the range of usually from about $-20°$ to about $120°$ C., preferably from about $-10°$ to about $30°$ C. in an atmosphere of preferably an inert gas.

After the irradiation, the solution is kept in the atmosphere of the inert gas at temperatures from room temperature to the reflux temperature, preferably the reflux temperature for 1 to 2 hours to afford $1\alpha,25$-dihydroxy-26,27-dimethylcholecalciferol.

The product can be separated from the reaction mixture and purified by a method known per se, such as chromatography, extraction or recrystallization.

$1\alpha,25$-Dihydroxy-26,27-dimethylocholecalciferol provided by this invention has very high vitamin D activity and is excellent in function to increase calcium absorption and retention in mammal bodies, and less toxic. Accordingly, the compound of this invention is useful as a medicament for the prevention and/or treatment of varying diseases caused by abnormality and disorders of calcium balance and calcium absorption, such as calcium pathobolism, osteoporosis, etc.

The excellent activity of the comound in this invention can be substantiated by the following animal test.

Test method

Wistar rats (Charles River: 3 weeks old) were put on a vitamin D-deficient diet for 3 weeks. To each of the rats was administered 0.05 ml of an ethanol solution of $1\alpha,25$-dihydroxy-26,27-dimethylcholecalciferol in this invention in an amount indicated in Table 1. After 24 hours from the administration, a blood was collected from the abdominal aora of the rat under ether anesthesia. The obtained blood was centrifuged at 3000 rpm for 10 minutes, and the amount of calcium in the resulting serum was determined by an atomic absorption method and the amount of an inorganic phosphorus by a FiskeSubbarrow method (Fiske, C. H. and Subbarrow, Y : J. Biol. Chem. 66 375(1925), respectively, The results are shown in Table 1. The atomic absorption device used is Shimazu Double Beam Atomic-Absorption Spectrophotometer AA-650, and the device used in the FiskeSubbarrow method is a Hitachi 500 Model automatic analyzer.

Test results $1\alpha,25$-Dihydroxy-26,27-dimethyl vitamin $D_3$ [compound I] of this invention showed the large amount of calcium and the increase in the amount of the inorganic phosphorus compared with $1\alpha,25$-dihydroxy vitamin $D_3$ [compound II], an active form of vitamin $D_3$.

TABLE 1

| Mendicament | Dose pmols/rat | Amonut of calcium mg/dl | Amount of inorganic phosphorus mg/dl |
| --- | --- | --- | --- |
| Ethanol alone | — | 9.24 ± 0.12 | 8.05 ± 0.34 |
| Compound I | 650 | 11.46 ± 0.20 | 10.38 ± 0.20 |
| (this invention) | 100 | 10.49 ± 0.22 | 9.63 ± 0.24 |
| Compound II | 3000 | 10.63 ± 0.29 | 9.81 ± 0.25 |
| (control) | 650 | 9.90 ± 0.01 | 9.10 ± 0.30 |

When the compound of this invention is used as a medicament for the prevention and/or treatment of diseases such as calcium pathobolism and osteoporosis it can be administered to mammals in a dose of about 25 to about 400 ng/day, preferably about 50 to about 200 ng/day. However, the above dose range is a provisional criterion and the compound can be administered in a dose deviated from the above range by the doctor's judgement depending on patients, degrees of diseases, sex, age and weight. The administration can be effected orally or parenterally through various routes (e.g. subcutaneous, intramuscular, intravenous, intraperitoneal, and intrarectal).

Thus, the compound of this invention can be formulated into a dosage form according to a dosage route. For example, for the oral administration, it can be formulated into dosage forms such as tablets, capsules, granules, powders, syrups and elixers. For the parenteral administration, it can be formulated into dosage forms such as injections, drops and suppositories. The pharmaceutical composition of such dosage form can be pepared by mixing an effective amount of the compound of this invention with a pharmaceutically acceptable carrier or diluent (adjuvant) and formulating the mixture into a desirous dosage form in a usual manner.

Illustrative of the adjuvant which may be incorporated into solid preparations such as tablets, capsules, granules, powders, etc. are a binder such as gum tragacanth, acacia, corn starch, or gelatin; an excipient such as dicalcium phosphate, a disintegrating agent such as corn starch, potato starch, algenic acid, and the like; a lubricant such as magnesium stearate; a sweetening agent such as sucrose, lactose, or saccharin; a flavoring agent such as peppermint, oil of wintergreen, or cherry. Various other materials may be present as coatings or to otherwise modify the physical form of the dosage unit. For instance, tablets may be coated with shellac, sugar, or both. A syrup or elixir may contain the active compound, sucrose as a sweetening agent, methyl and propyl parabens as presevartives, a dye, and in flavoring such as cherry or orange flavor.

Steril compositions for injection can be formulated according to conventional pharmaceutical practice by dissolving or suspending the active substance in a vehicle, such as water for injection, a naturally occurring vegetable oil, such as sesame oil, coconut oil, peanut oil, cottonseed oil, and the like, or a synthetic fatty vehicle such as ethyl oleate or the like. Buffers, preservatives, antioxidants and the like can be incorportated as required.

The following Examples illustrate this invention in more detail.

EXAMPLE

Synthesis of $1\alpha,25$-dihydroxy-26,27-dimethylcholecalciferol

[Compound I]

A solution of 3.5 mg (7.88 mmols) of 26,27-dimethyl-cholesta-5,7-diene-$1\alpha,3\beta,25$-triol in a solvent mixture of 90 ml benzene and 40 ml ethanol was irradiated at 0° C. for 5 minutes with a light of a medium-pressure mercury lamp (200 W) through a Vycor filter under an argon atmosphere.

After the irradiation, the solution was refluxed for 1 hour under an argon atmosphere. After the reflux, the solvent was distilled off from the resulting solution, and the thus obtained crude product was purified by thin layer chromatography (benzene/ethyl acetate=2/1, developed 4 times, Rf=0.21) to afford 0.8 mg of $1\alpha,25$-dihydroxy-26,27-dimethylcholecalciferol (yield 23%).

UV $\lambda_{max}^{EtOH}$: 265nm, 228 nm.

MS m/e: 426 (M+—$H_2O$, 10%), 408 (100), 390 (60), 269 (5.0), 251 (47), 157 (38), 152 (1.8), 134 (12), 116 (16).

26,27-Dimethylcolesta-5,7-diene-$1\alpha,3\beta,25$-triol can be produced as follows:

(A) $1\alpha,3\beta$-Diacetoxy-26,27-dinorcholest-5-en-24-al (Compound C)

To a solution of 650 mg (1.42 mmols) of $1\alpha,3\beta$-diacetoxychol-5-en-24-ol in 35 ml of methylene chloride was added 750 mg (3.48 mmols) of pyridinium chlorochromate, and the resulting mixture was stirred at room temperature for 2 hours. Subsequently, 100 ml of ether was added to the mixture and the solution was eluted through a column filled with 15 g of Florisil to give 550 mg of $1\alpha,3\beta$-diacetoxychol-5-en-24-al (Compound B).

Thereafter, n-butyl lithium (1.5M solution in hexane, 1.5 ml) was added to a solution of 750 mg (2.19 mmols) of methoxymethyltriphenyphosphonium choloride in 5 ml of tetrahydrofuran at −10° C., and the resulting solution was stirred at room temperature for 5 minutes. To the solution was added a solution of 550 mg of the above obtained compound B in 5 ml of tetrahydrofuran, and the mixture was stirred at room temperature for 1 hour. Subsequently, the reaction was quenched by addition of water, and the mixture was extracted with ethyl acetate. The extract was washed with water, dired and evaported to dryness.

To the resulting crude product were added 5 ml of pyridine and 4 ml of acetic anhydride, and the mixture was stirred at 60° C. for 1 hour. Thereafter, in the same way as above, the reaction mixture was diluted with ethyl acetate. The whole was washed with water and dried, and the solvent was evaporated. The thus obtained crude product was purified through column chromatography (silica gel 30 g, benzene/ethyl acetate=50/1) to give 271 mg of $1\alpha,3\beta$-diacetoxy-25-methoxy-26,27-dinorcholesta-5,24-diene.

To a solution of 271 mg of the compound in 8 ml of dioxane was added 2 ml (3.6M) of sulfuric acid, and the mixture stirred at room temperature for 6 hours. The reaction mixture was diluted with ethyl acetate, and the whole was washed with water, dried and concentrated to dryness. The thus obtained crude product was purified by column chromatography (silica gel 30 g, benzene/ethyl acetate=50/1) to give 120 mg of the above-identified compound C as an oil (yield 18.0%).

NMR (CDCl$_3$)δ: 0.65 (3H, s, 18—H$_3$), 0.90 (3H, d, J=6 Hz, 21—H$_3$), 1.07 (3H, s, 19—H$_3$), 2.01 (3H, s, acetyl), 2.04 (3H, s, acetyl), 4.90 (1H, m, 3—H), 5.04 (1H, m, 1—H), 5.50 (1H, m, 6—H), 9,77 (1H, t, J=2 Hz, 25—H).

(B) 1α,3β-Diacetoxy-26,27-dinorcholest-5-en-25-oic acid methyl ester (Compound E)

To a solution containing 120 mg (0.254 mmol) of 1α,3β-diacetoxy-26,27-dinorcholest-5-en-25-al (compound C) obained in (A) and 5 ml of acetone was added an equimolar amount of Jones reagent, and the mixture was stirred for 5 minutes. The resulting reaction mixture was diluted with ether. The whole was washed with water and dried, and the solvent was evaporated.

The resulting crude 1α,3β-diacetoxy-26,27-dinorcholest-5-en-25-oic acid (compound D) was dissolved in 5 ml of ether, and an excess amount of diazomethane solution was added to the mixture. The ether solution was stirred at room temperature for 5 minutes. After the solvent was evaporated from the resulting solution, the residue was purified by column chromatography (silica gel 10 g, hexane/ethyl acetate=4/1) to afford 101 mg of the above-identified compound E as an oil (yield 79%).

NMR(CDCl$_3$)δ: 0.65 (3H, s, 18—H$_3$) 0.90 (3H, d, J=6 Hz, 21—H$_3$) 1.07 (3H, s, 19—H$_3$) 2.01 (3H, s, acetyl) 2.04 (3H, s, acetyl) 3.66 (3H, s, —CO$_2$CH$_3$) 4.90 (1H, m, 3—H) 5.04 (1H, m, 1—H) 5.50 (1H, m, 6—H)

(C) 1α, 3β-Diacetoxy-26, 27-dimethylcholest-5-en-25-ol (Compound F)

To a solution containing 45 mg (0.0896 mmol) of 1α, 3β-diacetoxy-26,27-dinorcholest-5-en-25-oic acid methyl ester (Compound E) obtained in (B) and 5 ml of tetrahydrofuran was added 0.1 ml of a 3M ether solution of ethylmagnesium bromide. The mixture was stirred at room temperature for 1 hour. Thereafter, the reaction mixture was poured into a large amount of water. The mixture was then extracted with ethyl acetate. The extract was washed with water, dried and the solvent was evaporated. To the resulting residue were added 0.5 ml of pyridine and 0.5 ml of acetic anhydride, and the mixture was stirred overnight at room temperature. The resulting reaction mixture was diluted with ethyl acetate. The whole was washed with water and dried, and the solvent was evaporated. The thus obtained residue was purified through column chromatography (silica gel 10 g, hexane/ethyl acetate32 5/1) to afford 34 mg of the above-identified compound F as an oil (yield 72%).

NMR(CDCl$_3$)δ: 0.65 (3H, s, 18—H$_3$), 0.86 (6H, t, J=7 Hz, 26— and 27—CH$_3$), 0.90 (3H, d, J=6 Hz, 21—H$_3$), 10.7 (3H, s, 19—H$_3$), 2.01 (3H, s, acetyl), 2.03 (3H, s, acetyl), 4.90 (1H, m, 3—H), 5.03 (1H, m, 1—H), 5.48 (1H, m, 6—H).

(D) 26,27-Dimethylcholesta-5,7-diene-1α,3β-25-triol (Compound H)

A carbon tetrachloride solution containing 16 mg (0.0302 mmol) of 1α,3β-diacetoxy-26,27-dimethylcholest-5en-25-ol obtained in (C) and 7.5 mg (0.0421 mmol) of N-bromosuccinimide was refluxed in an argon atmosphere for 20 minutes. The precipitates formed by cooling the resulting solution to 0° C. were separated by filtration. The filtrate was concentrated under reduced pressure below 40° C. to afford the 7-position brominated compound G.

The crude bromide was dissolved in 4 ml of tetrahydrofuran, and a catalytic amount of tetra-n-butylammonium bromide was added, followed by stirring at room temperature for 50 minutes. Further, to the tetrahydrofuran solution was added 0.1 mol of a 1M tetrahydrofuran solution of tetra-n-butylammonium fluoride, and the mixture was stirred at room temperature for 30 minutes in an argon atmosphere. The resulting reaction mixture was diluted with ethyl acetate, and the whole was washed with water, dried and concentrated to dryness.

To a solution of the resulting crude 1α,3β-diacetoxy-26,27-dimethylcholesta-5,7-dien-25-ol in 4 ml of tetrahydrofuran was added 2 ml of a 5% potassium hydroxide-methanol solution, and the mixture was stirred overnight at room temperature. The thus obtained reaction mixture was diluted with ethyl acetate, and the whole was washed with water, dried and evaporated. The resulting residue was purified through thin layer chromatography (benzene/ethyl acetate=2/1, developed 6 times, Rf=0.27) to afford 3.5 mg of the above-identified compound H (yield 26%).

UV λ$_{max}^{ethanol}$ 272, 282, 294 nm.

What we claim is:
1. 1α,25-Dihydroxy-26,27-dimethylcholecalciferol represented by formula:

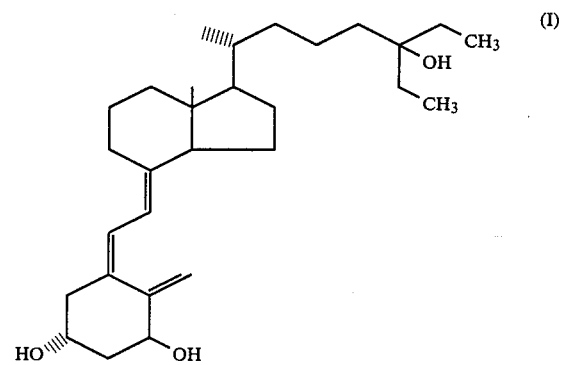

2. A pharmaceutical composition for the prevention or treatment of calcium pathobolism or osteoporosis, which comprises an amount, effective for the prevention or treatment of said diseases, of 1α,25-dihydroxy-26,27-dimethylcholecalciferol, and a pharmaceutically acceptable diluent or carrier.

3. A method for the prevention or treatment of calcium pathobolism or osteoporosis, which comprises administering to a mammal an effective amount of 1α,25-dihydroxy-26,27-dimethylcholecalciferol.

* * * * *